United States Patent
Bor et al.

(10) Patent No.: US 11,896,304 B2
(45) Date of Patent: *Feb. 13, 2024

(54) IN VIVO PRE-SURGICAL CHARACTERIZATION OF CATARACTOUS LENSES

(71) Applicant: Alcon Inc., Fribourg (CH)

(72) Inventors: Zsolt Bor, San Clemente, CA (US); Mikhail Ovchinnikov, Dana Point, CA (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/179,203

(22) Filed: Mar. 6, 2023

(65) Prior Publication Data
US 2023/0255471 A1 Aug. 17, 2023

Related U.S. Application Data

(63) Continuation of application No. 17/205,470, filed on Mar. 18, 2021, now Pat. No. 11,617,506, which is a
(Continued)

(51) Int. Cl.
*A61B 8/10* (2006.01)
*A61B 5/00* (2006.01)
(Continued)

(52) U.S. Cl.
CPC .......... *A61B 3/0025* (2013.01); *A61B 5/0059* (2013.01); *A61B 8/00* (2013.01);
(Continued)

(58) Field of Classification Search
CPC ....... A61B 5/0075; A61B 3/00; A61B 3/0008; A61B 3/0025; A61B 3/10; A61B 3/1173; A61B 3/1176; A61B 8/10
See application file for complete search history.

(56) References Cited

U.S. PATENT DOCUMENTS

2013/0345807 A1* 12/2013 Olsen ........................ A61F 2/16
623/6.11
2014/0320805 A1* 10/2014 Wilzbach .................. A61F 2/16
351/204

FOREIGN PATENT DOCUMENTS

RU 2642216 C1 * 1/2018
RU 2647788 C2 * 3/2018

OTHER PUBLICATIONS

Qinar, Yasin, Abdullah Kur§at Cingu, Muhammed Qahin, Alparslan Qahin, Harun Yuksel, Fatih Mehmet Turkcu, Tuba Qinar, and ihsan Qaga. "Comparison of optical versus ultrasonic biometry in keratoconic eyes." Journal of ophthalmology 2013 (2013).*
(Continued)

*Primary Examiner* — Carolyn A Pehlke

(57) ABSTRACT

Systems and methods are provided for in vivo pre-surgical characterization of lenses, such as cataractous lenses. A method comprises obtaining an electromagnetically-measured value related to the axial thickness of the lens, obtaining an ultrasound-measured value related to the axial thickness of the lens, calculating a relationship value based upon the electromagnetically-measured value and the ultrasound-measured value, and determining a mechanical property value based upon the calculated relationship value. The mechanical property may relate to lens hardness, rigidity, or density, or the amount of energy for a phacoemulsification procedure. A system may comprise an optical interferometer for measuring data to obtain the electromagnetically-measured value and an ultrasound biometer for measuring data to obtain the ultrasound-measured value.

9 Claims, 5 Drawing Sheets

Related U.S. Application Data continuation of application No. 15/958,956, filed on Apr. 20, 2018, now Pat. No. 10,973,404.

(60) Provisional application No. 62/500,292, filed on May 2, 2017.

(51) Int. Cl.
*A61B 3/00* (2006.01)
*A61F 9/008* (2006.01)
*A61F 9/00* (2006.01)
*A61F 2/16* (2006.01)
*A61B 8/00* (2006.01)

(52) U.S. Cl.
CPC ............... *A61B 8/10* (2013.01); *A61F 2/16* (2013.01); *A61F 9/008* (2013.01); *A61F 9/0017* (2013.01); *A61F 2009/0087* (2013.01); *A61F 2009/00855* (2013.01); *A61F 2009/00887* (2013.01)

(56) References Cited

OTHER PUBLICATIONS

Haigis, Wolfgang, Barbara Lege, Nicile Miller, and Brita Schneider Comparison of inversion ultrasound biometry and partial coherence interferometry far intraocular lens calculation according to Haigis. Graete's archive for clinical and experimental ophthalmology 238, No. 3 (2000): 785-779).*

* cited by examiner

IN VIVO PRE-SURGICAL CHARACTERIZATION OF CATARACTOUS LENSES

CROSS-REFERENCE TO RELATED APPLICATIONS

This application is a continuation of prior application Ser. No. 17/205,470, filed Mar. 18, 2021, which is a continuation of prior application Ser. No. 15/958,956, filed Apr. 20, 2018, which claims the benefit of U.S. provisional application No. 62/500,292, filed May 2, 2017, the entire contents of each being incorporated herein by reference.

FIELD OF THE INVENTION

This disclosure relates generally to systems and methods for the characterization of eye lenses, in particular to systems and methods for the characterization of cataractous lenses.

BACKGROUND OF THE INVENTION

A cataract is a clouding of the lens in the eye. Cataracts can cause impaired vision, including clouded, dim, or blurry sight, and increased sensitivity to light.

Cataracts are commonly treated by cataract surgery. The most prevalent cataract surgery involves removing the cataractous lens and replacing it with a clear synthetic lens or intraocular lens (IOL). Cataract surgery is typically performed as an outpatient procedure.

In phacoemulsification cataract surgery, a small incision is made in the cornea of the eye and an ultrasonic probe is inserted through the incision to the lens. The vibration of the ultrasonic probe at ultrasonic frequency causes the lens to fragment into tiny pieces. The lens fragments are aspirated away, and an IOL is implanted into the lens capsule in place of the cataractous lens.

While phacoemulsification is the most commonly-performed form of cataract surgery, in some cases extracapsular cataract extraction (ECCE) is performed. In ECCE, the entire cataractous lens is removed and replaced with the IOL. ECCE typical requires a larger incision than phacoemulsification and can require more recovery time. In many cases, ECCE is performed because the facility does not have the equipment for phacoemulsification, often due to the cost associated with such equipment. In some cases, ECCE is chosen because the cataractous lens is so hard that it would be difficult to fragment effectively through phacoemulsification.

Prior to performing cataract surgery, the physician examines the eye to obtain information for the procedure. For example, the physician performs certain measurements in order to select the appropriate IOL.

It may also be desirable for the physician to have information about the hardness of the cataractous lens in order to determine whether the patient is a suitable candidate for phacoemulsification and, if so, to determine a suitable phacoemulsification energy to be utilized during the procedure. Such information can be helpful to improve outcome, so that the physician does not use insufficient energy or excess energy to fragment the lens, which can lead to complications such as insufficient fragmentation, excess fragmentation, extended procedure time, damage to the lens capsule, damage to other parts of the eye, or extended recovery time.

There are a number of methods that have been used to obtain a pre-surgical characterization of cataractous lenses based on optical properties and visual appearance. For example, methods that have been used include slit lamp appearance (e.g., LOCSIII), backward light scattering (e.g., anterior chamber OCTs), lateral light scattering (e.g., PENTACAM from Oculus and GALILEI from Ziemer Group), and forward light scattering (e.g., OQAS HD ANALYZER from Visiometrics and C-QUANT from Oculus). However, the correlation between these optical properties and mechanical properties can be relatively weak, making it difficult to accurately determine lens hardness from such techniques.

In the past, proposals have been made in efforts to measure the hardness of cataractous lenses. For example, it has been proposed to obtain ultrasound measurements of the lens and to derive a proposed measure of lens hardness based upon the ultrasound readings for the first lens peak, the last lens peak, and the time of flight between the lens peaks (See M. El-Brawany, Ultrasound-Based Noninvasive Measurement of Cataract Hardness, The Online Journal on Electronics and Electrical Engineering, vol. 2, no. 2, pp. 246-249 (2009)). Similarly, it has been proposed to characterize lens hardness based upon ultrasound velocity or ultrasound attenuation (See D. Jesus, Ultrasound Techniques for Lens Hardness Characterization: A Comparison Study, 2012 IEEE International Ultrasonics Symposium Proceedings, pp. 2376-2379 (2012)).

Prior proposals have had drawbacks such as an inability or difficulty to obtain reliable or useful data in vivo, an unreliability of the calculations, insufficient correlation of the calculations to information useful for the cataract surgery procedure, and/or little or no clinical adoption.

SUMMARY OF THE INVENTION

The inventions described herein provide systems and methods for the characterization of eye lenses, in particular systems and methods for the characterization of cataractous lenses.

In some embodiments, systems and/or methods are provided for obtaining a pre-surgical characterization of a lens of a human or animal eye prior to eye surgery. The systems and/or methods take measurements in vivo and non-invasively. The systems and/or methods take those measurements to determine a mechanical property value related to one or more mechanical properties of the lens, such as hardness, rigidity, and/or density, and/or the amount of phacoemulsification energy needed in a phacoemulsification procedure.

In some embodiments, the systems include a first device using light, such as laser light, or other electromagnetic energy for taking measurements to obtain a first value related to the axial thickness of the lens. Thus, the systems include a first device for obtaining a first value related to the axial thickness of the lens without using ultrasound. The electromagnetically-measured value may be an electromagnetically-measured value for the axial thickness of the lens. The systems also include a second device using ultrasound for taking measurements to obtain a second value related to the axial thickness of the lens. The ultrasound-measured value may be, for example, an ultrasound-measured estimated value for the axial thickness of the lens based upon an assumed velocity of the ultrasound signal. As another example, the ultrasound-measured value may be an ultrasound-measured value for the time of ultrasound travel through the lens.

The first device may be an optical interferometer, wherein the optical interferometer is adapted to transmit electromagnetic energy into the lens of the eye and to capture reflected signals of that electromagnetic energy. The reflected signals of that electromagnetic energy may be used to obtain an electromagnetically-measured value related to the axial thickness of the lens. In some embodiments, the electromagnetic energy transmitted by the optical interferometer is laser light.

The second device may be an ultrasound biometer, wherein the ultrasound biometer is adapted to transmit an ultrasound signal into the lens of the eye and to capture reflected signals of that ultrasound signal. The reflected signals of that ultrasound signal may be used to obtain an ultrasound-measured value related to the axial thickness of the lens. In some embodiments, the ultrasound biometer is an A-scan ultrasound biometer.

The systems may calculate a relationship value based upon the light-measured (or electromagnetically-measured) value related to the axial thickness of the lens and the ultrasound-measured value related to the axial thickness of the lens. For example, the relationship value may be a ratio of the light-measured (or electromagnetically-measured) value to the ultrasound-measured value. In one embodiment, the relationship value is a ratio of the electromagnetically-measured value to the ultrasound-measured value, wherein the electromagnetically-measured value is an electromagnetically-measured value for the axial thickness of the lens, and the ultrasound-measured value is an ultrasound-measured estimated value for the axial thickness of the lens based upon an assumed velocity of the ultrasound signal. In another embodiment, the relationship value is a ratio of the electromagnetically-measured value to the ultrasound-measured value, wherein the electromagnetically-measured value is an electromagnetically-measured value for the axial thickness of the lens, and the ultrasound-measured value is an ultrasound-measured value for the time of ultrasound travel through the lens. The relationship value may also be the inverse of such ratios. The systems may use the calculated relationship value to determine a mechanical property value based upon the calculated relationship value, wherein the mechanical property value is related to a mechanical property of the lens, such as lens hardness, rigidity, or density, or the amount of phacoemulsification energy needed in a phacoemulsification procedure.

The systems may include a calculation module comprising computer code stored in memory of the system and executable by one or more processors of the system, the calculation module configured to calculate the relationship value based upon the electromagnetically-measured value related to the axial thickness of the lens and the ultrasound-measured value related to the axial thickness of the lens. The calculation module also may be configured to determine the mechanical property value based upon the calculated relationship value, wherein the mechanical property value is related to a mechanical property of the lens, such as lens hardness, rigidity, or density, or the amount of phacoemulsification energy needed in a phacoemulsification procedure.

In some embodiments, the methods include use of systems as described herein. The methods include obtaining a first electromagnetically-measured value related to the axial thickness of the lens and obtaining a second ultrasound-measured value related to the axial thickness of the lens. The methods may calculate a relationship value based upon the electromagnetically-measured value related to the axial thickness of the lens and the ultrasound-measured value related to the axial thickness of the lens. The methods may use the calculated relationship value to determine a mechanical property value based upon the calculated relationship value, wherein the mechanical property value is related to a mechanical property of the lens, such as lens hardness, rigidity, or density, or the amount of phacoemulsification energy needed in a phacoemulsification procedure.

The mechanical properties of a lens, such as lens hardness, rigidity, or density, or the amount of phacoemulsification energy needed in a phacoemulsification procedure, are affected by cataracts. An alteration of the mechanical properties of a lens by cataracts alters the speed of ultrasound through a lens. Thus, by obtaining an electromagnetically-measured value and an ultrasound-measured value as described herein, one can evaluate the effect of the lens on ultrasound transmission, and from that information determine one or more mechanical properties of the lens.

DETAILED DESCRIPTION

Figure 1:
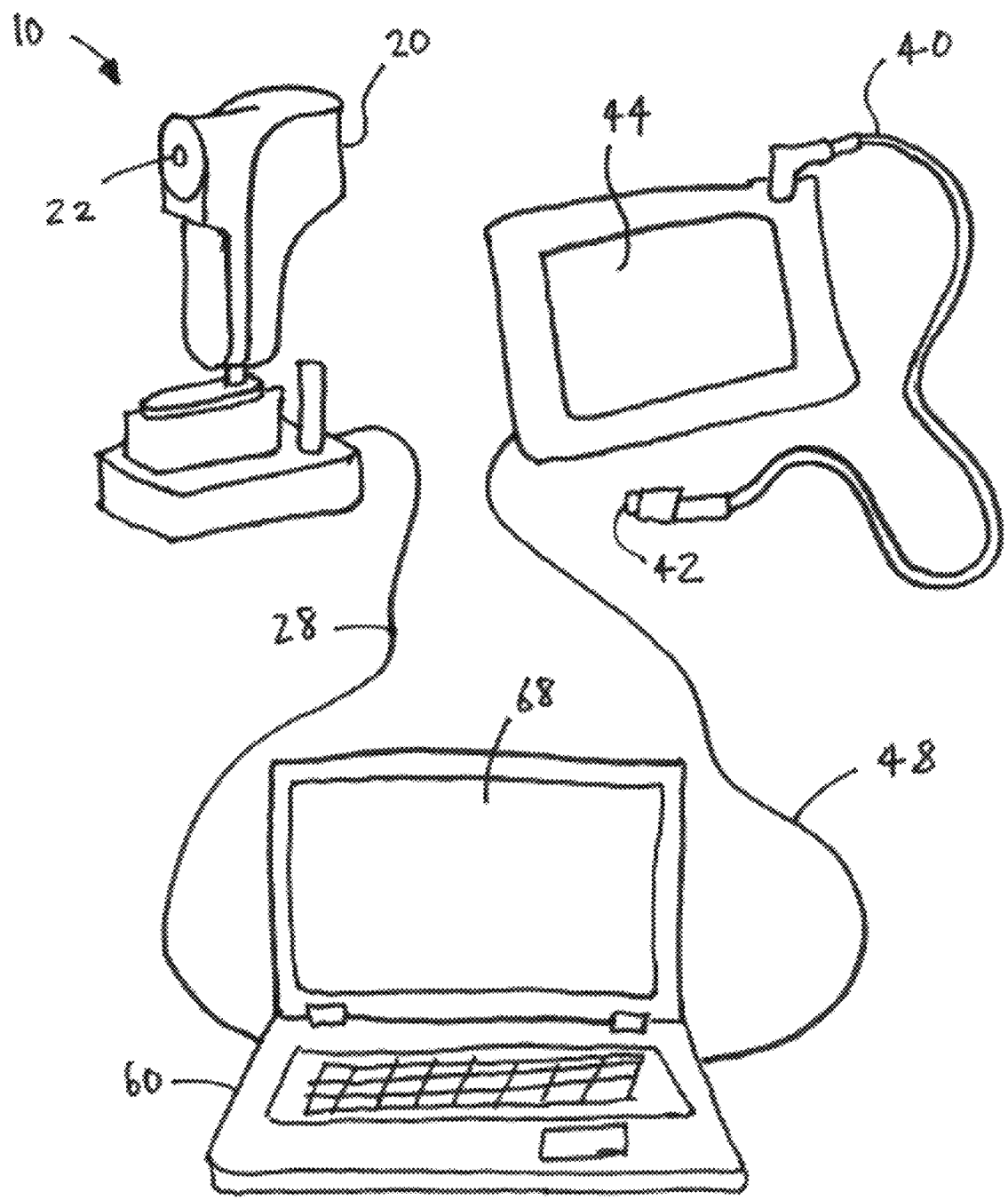
FIG. 1 shows an example of a system for obtaining a pre-surgical characterization of a lens.

FIG. 1 shows an example of a system 10 for obtaining a pre-surgical characterization of a lens of a human or animal eye prior to eye surgery, such as cataract surgery.

In this example, the system 10 includes a first device 20 for using light, such as laser light, or other electromagnetic energy, to obtain a first electromagnetically-measured value related to the axial thickness of the lens. The first device 20 may be an optical interferometer, such as, for example, a LENSTAR device from Haag-Streit Diagnostics. As one example, the first device 20 may be a LENSTAR LS 900 device from Haag-Streit Diagnostics. The first device 20 as shown includes an optical transmission and reception location 22 through which electromagnetic energy is transmitted into the eye and received.

The first device 20 is adapted to transmit electromagnetic energy into the lens of the eye and to capture reflected signals of that electromagnetic energy. The reflected signals of that electromagnetic energy may be used to obtain an electromagnetically-measured value related to the axial thickness of the lens. In the example of the first device 20, the electromagnetic energy transmitted by the optical interferometer is laser light. The first device 20 obtains the first electromagnetically-measured value without using ultrasound.

The system 10 also includes a second device 40 for using ultrasound to obtain a second value related to the axial thickness of the lens. The second device 40 may be an ultrasound biometer, wherein the ultrasound biometer is adapted to transmit an ultrasound signal into the lens of the eye and to capture reflected signals of that ultrasound signal. The second device 40 may be an A-scan ultrasound biometer, such, for example, a PALMSCAN device from Micro Medical Devices. The second device 40 as shown includes an ultrasound transmission and reception tip 42 through which ultrasound signals are transmitted into the eye and received. The second device 40 in this example includes an optional display 44.

The system 10 further includes a computer 60 which may include components such as one or more processors, memory devices, input devices such as a keyboard, computer mouse and/or track pad, and a display 68. The first device 20 may be connected to the computer 60 to provide input to the computer 60, such as by a connection cable 28. Alternatively, the first device 20 may have its own display or output, and a user may take data output from the first device 20 and may input that data into the computer 60, such as manually or by removable storage such as a USB drive. The second device 40 also may be connected to the computer 60 to provide input to the computer 60, such as by a connection cable 48. Alternatively, the second device 40 may have its own display or output, and a user may take data output from the second device 40 and may input that data into the computer 60, such as manually or by removable storage such as a USB drive.

The first device 20 may have its own computing capabilities, including one or more of its own processors and/or memory devices, as well as its own display. Alternatively, the first device 20 may utilize the processing, memory, and/or display capabilities of the computer 60. The second device 40 also may have its own computing capabilities, including one or more of its own processors and/or memory devices, as well as its own display. Alternatively, the second device 40 may utilize the processing, memory, and/or display capabilities of the computer 60.

Figure 2:
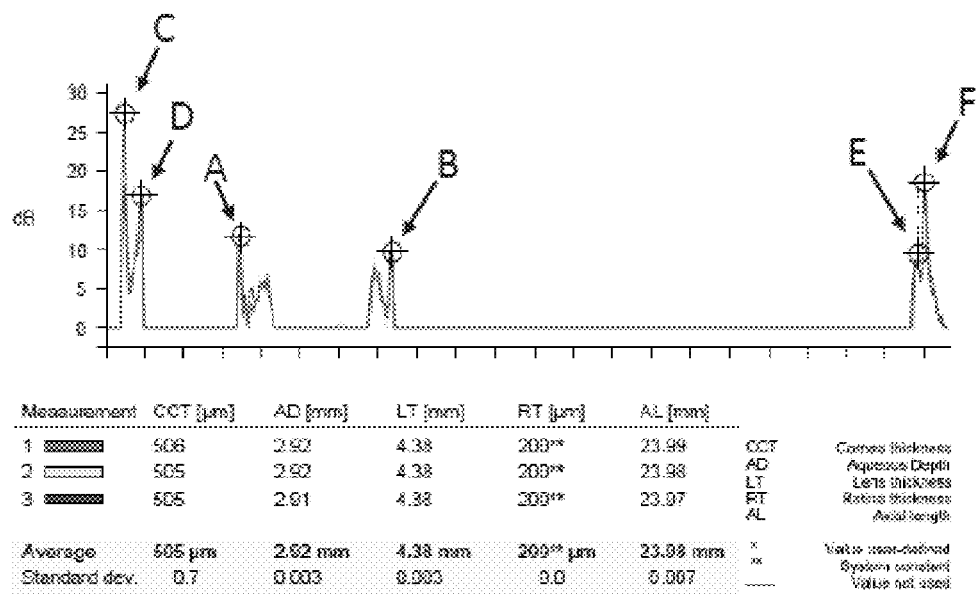
FIG. 2 shows an example of output from an optical device for obtaining an electromagnetically-measured value.

FIG. 2 shows an example of output from the first device 20, which may be displayed, for example, on a display of the computer 60 or on a display of the first device 20 itself. FIG. 2 shows the interferometer measurements of signal strength (y-axis) as a function of time or distance (x-axis). The peaks on the graph are associated with different places in the eye. For example, peaks A and B are associated with the front and back of the lens, respectively; peaks C and D are associated with the front and back of the cornea, respectively; and peaks E and F are associated with the front and back of the retina, respectively.

The distances between peaks can be used to calculate values for distances in the eye. The refractive index in the lens can be generally regarded as 1.41, and this refractive index is generally considered as not influenced significantly by the development of cataracts. Using the measurements from the first device 20, the system 10 can obtain an electromagnetically-measured first value for the axial lens thickness along the axis of the eye. Other values related to the axial lens thickness may be used as the first value (or electromagnetically-measured value). The first value (or electromagnetically-measured value) can be determined in one or more processors of the system, including one or more processors of the computer 60, the first device 20, and/or the second device 40.

Figure 3:
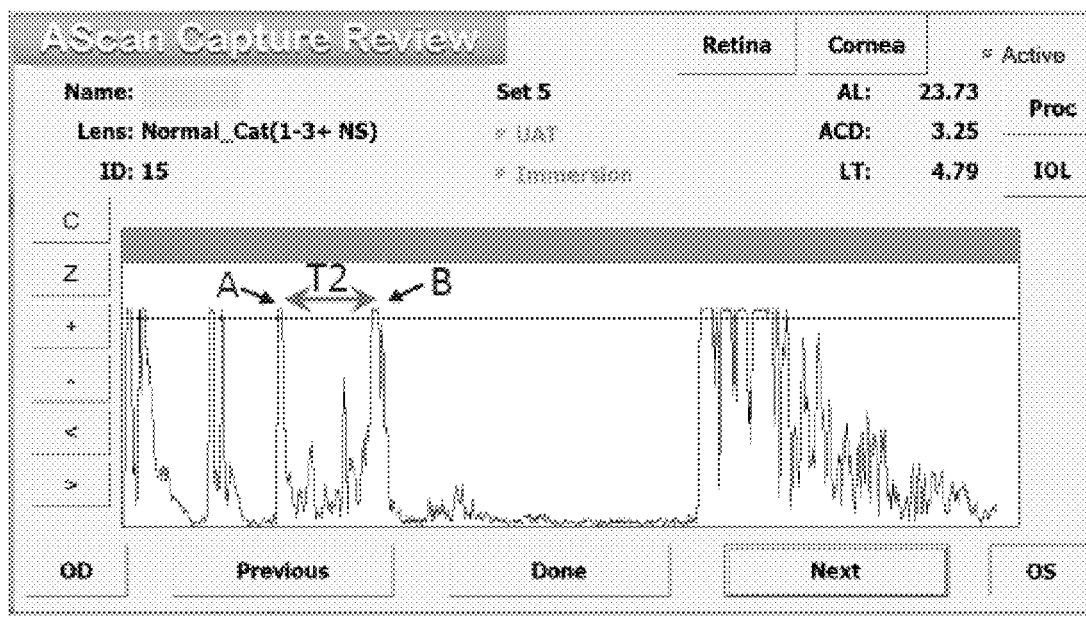
FIG. 3 shows an example of output from an ultrasound device for obtaining an ultrasound-measured value.

FIG. 3 shows an example of output from the second device 40, which may be displayed, for example, on a display of the computer 60 or on a display of the second device 40 itself. FIG. 3 shows the ultrasound measurements of signal strength (y-axis) as a function of time or distance (x-axis). The peaks on the graph are associated with different places in the eye. For example, peaks A and B are associated with the front and back of the lens, respectively.

For the second device 40, which in this example is an ultrasound biometer, the distances between peaks can be used to calculate values for distances in the eye, using the relationship $D2=T2*v$, where D2 is distance, T2 is time, and v is the ultrasound velocity. In one example, an assumed velocity of the ultrasound signal may be used for the value v. For example, an assumed velocity of 1641 meters per second can be used for the value v, which is a value for the propagation of ultrasound in a healthy human lens. Using the formula $D2=T2*v$, and the assumed velocity of the ultrasound signal, the system 10 can calculate a second value, or ultrasound-measured estimated value, for the axial thickness of the lens. The time between the peaks A and B is marked on the graph as time T2. In this embodiment, using this time T2, and the value v for the assumed velocity of the ultrasound signal, the system 10 obtains the distance D2, representing a second value, or ultrasound-measured estimated value, for the axial thickness of the lens.

In the example in which the ultrasound-measured value is an ultrasound-measured estimated value for the axial thickness of the lens, computed from the formula $D2=T2*v$, wherein v is an assumed velocity of the ultrasound signal, it can be expected that the ultrasound-measured estimated value for the axial thickness of the lens in a cataractous lens will be different from the actual thickness of the lens, due to the assumed ultrasound velocity being different from the actual ultrasound velocity in the cataractous lens. For example, in a cataractous lens, it can be expected that the actual ultrasound velocity through the lens will be higher than 1641 meters per second, because the cataract alters the hardness, rigidity, and density of the lens and therefore alters the ultrasound speed through the lens. Accordingly, in a lens hardened by cataracts, if 1641 meters per second is the assumed velocity, the resulting value D2 representing the ultrasound-measured estimated value of lens thickness will be less than the actual lens thickness and less than the electromechanically-measured value of lens thickness. The amount of the difference is related to the amount of the hardness, rigidity, or density of the lens. Accordingly, the amount of the difference can be used to determine a value related to the hardness, rigidity, or density of the lens, as described below.

The second value (or ultrasound-measured value) may be another ultrasound-measured value aside from an ultrasound-measured estimated value for the axial thickness of the lens. In another embodiment, the second value (or ultrasound-measured value) may be the time T2 of ultrasound travel between the peaks A and B. As will be appreciated, this time T2 between the peaks A and B is an ultrasound-measured value related to the axial thickness of the lens, and hardness, rigidity, or density of the lens will affect the time T2 of ultrasound travel. Other values related to the axial lens thickness may be used as the second value (or ultrasound-measured value). The second value (or ultrasound-measured value) can be determined in one or more processors of the system, including one or more processors of the computer 60, the first device 20, and/or the second device 40.

Based upon the first, electromagnetically-measured value related to the axial thickness of the lens, and the second, ultrasound-measured value related to the axial thickness of the lens, the system 10 can calculate a relationship value. For example, the relationship value may be a ratio of the electromagnetically-measured (or light-measured) value to the ultrasound-measured value. In one embodiment, the relationship value is a ratio of the electromagnetically-measured value to the ultrasound-measured value, wherein the electromagnetically-measured value is an electromagnetically-measured value for the axial thickness of the lens, and the ultrasound-measured value is an ultrasound-measured estimated value for the axial thickness of the lens, computed from the formula $D2=T2*v$, wherein v is an assumed velocity of the ultrasound signal. In another embodiment, the relationship value is a ratio of the electromagnetically-measured value to the ultrasound-measured value, wherein the electromagnetically-measured value is an electromagnetically-measured value for the axial thickness of the lens, and the ultrasound-measured value is an ultrasound-measured value for the time of ultrasound travel through the lens, or T2. The relationship value may also be the inverse of these ratios, or another value that quantifies the effect on the ultrasound signal by comparing the ultrasound-measured value to the electromagnetically-measured value.

Because of the effect of the cataracts on ultrasound travel, the relationship value contains information related to mechanical properties of the lens. For example, if the relationship value is a ratio of the electromagnetically-measured value to the ultrasound-measured value, wherein the electromagnetically-measured value is an electromagnetically-measured value for the axial thickness of the lens, and the ultrasound-measured value is an ultrasound-measured estimated value for the axial thickness of the lens, computed from the formula $D2=T2*v$, wherein v is an assumed velocity of the ultrasound signal of 1641 meters per second (or another assumed velocity less than the actual ultrasound velocity through the cataractous lens), then for a cataractous lens the ultrasound-measured estimated value for lens thickness is less than the actual lens thickness, and the relationship value R can be expected to be a number greater than 1. The deviation of R from 1 is related to lens hardness, rigidity, and/or density, and/or the amount of phacoemulsification energy needed in a phacoemulsification procedure.

The system 10 is configured to use the calculated relationship value to determine a mechanical property value, wherein the mechanical property value is related to a mechanical property of the lens, such as lens hardness, rigidity, or density, or the amount of energy needed in a phacoemulsification procedure. The amount of energy needed may be an amount representative of the equivalent phaco time (EPT), representing the amount of time needed for the procedure at 100% power.

The correlation between the relationship value and the mechanical property may be established through data collection that may be performed prior to setting up the system. For example, a survey may be taken of actual patients and procedures wherein, for each patient, the necessary measurements are taken, a relationship value is calculated, and a mechanical property is evaluated. The mechanical property may be evaluated by testing or by physician or operator evaluation. For example, hardness, rigidity, and/or density measurements may be taken ex vivo on lenses extracted in an ECCE procedures. As another example, a physician may record the amount of phacoemulsification energy needed for a phacoemulsification procedure. Such a recordation may be, for example, of the equivalent phaco time (EPT), representing the equivalent amount of time for the procedure at 100% power.

Figure 4:
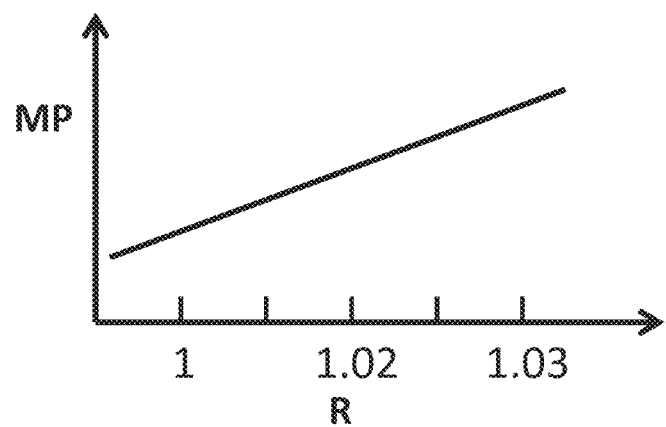
FIG. 4 shows an example curve fitting of a relationship value to a mechanical property value.

Once data is obtained for a set of patients for relationship values and the corresponding desired mechanical property, curve-fitting may be done to establish the relationship between the relationship values and the mechanical properties. FIG. 4 shows an example curve fitting of a relationship value R to a mechanical property MP such as mechanical hardness. Depending on the relationship values and mechanical properties, the curve-fit correlation may result in a function that is linear or non-linear. The correlation function may be programmed into the system 10 so that for any given relationship value, the system can use the correlation function to compute a corresponding value for the desired mechanical property. In addition to or as an alternative to curve-fitting, a database may be established associating relationship values and mechanical properties. The database may be programmed into the system 10 so that for any given relationship value, the system can use the database to look up and/or calculate (e.g., by interpolation) a corresponding value for the desired mechanical property.

Thus, the system 10 may include a calculation module comprising computer code stored in memory of the system 10, including in one or more memory devices of the computer 60, the first device 20, and/or the second device 40, with the computer code executable by one or more processors of the system 10, including in one or more processors of the computer 60, the first device 20, and/or the second device 40. The calculation module is configured to calculate the relationship value based upon the electromagnetically-measured value related to the axial thickness of the lens and the ultrasound-measured value related to the axial thickness of the lens. The calculation module is also configured to determine a mechanical property value based upon the calculated relationship value, wherein the mechanical property value is related to a mechanical property of the lens. The mechanical property of the lens may be lens hardness, rigidity, or density, or the amount of energy needed in a phacoemulsification procedure. The calculation module may determine that mechanical property value from a correlation function that correlates relationship values to mechanical property values. Additionally or alternatively, the calculation module may determine that mechanical property value by looking up or calculating (e.g., by interpolation) that mechanical property value from a database that correlates relationship values to mechanical property values.

Figure 5:
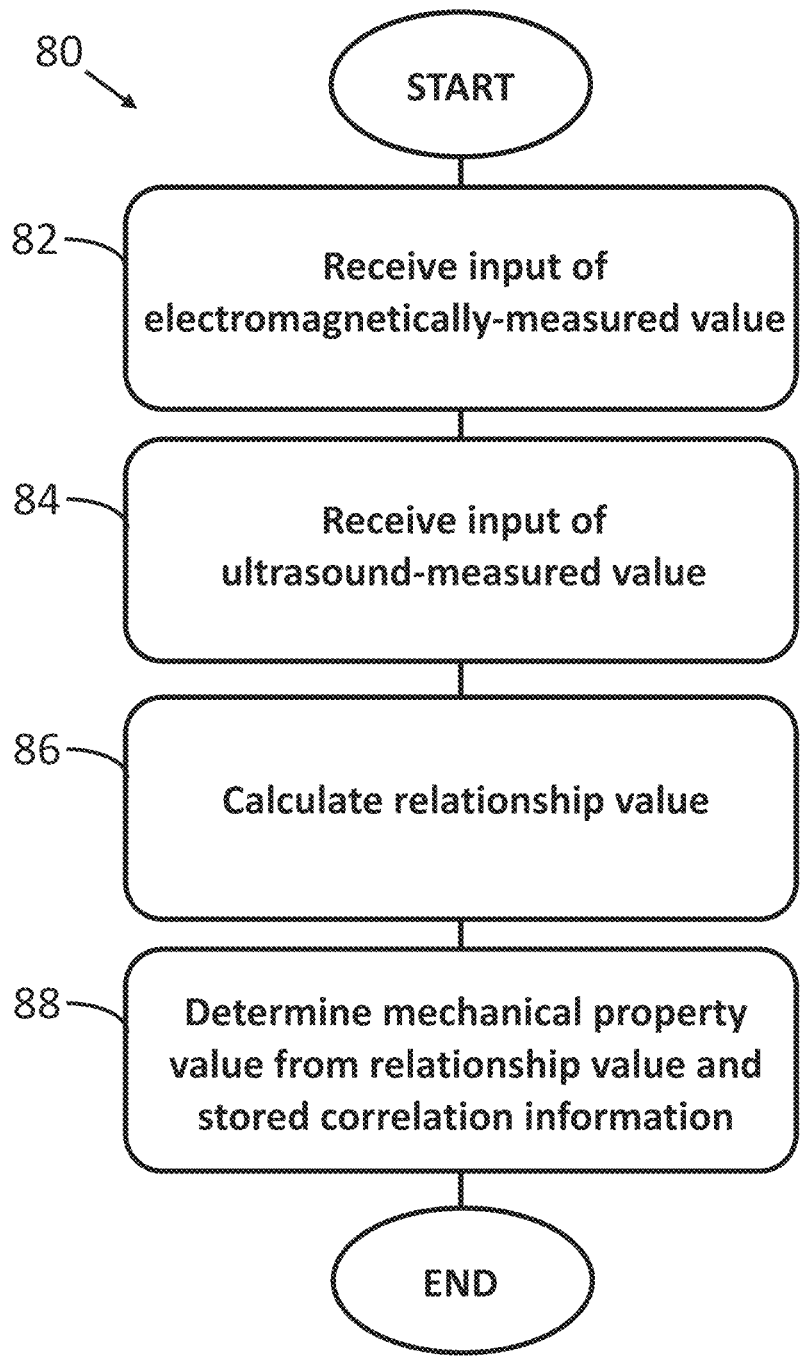
FIG. 5 shows a flowchart for steps in a first example of a calculation module.

FIG. 5 shows a flowchart for steps in a first calculation module 80. In a first step 82, the electromagnetically-measured value related to the axial thickness of the lens is received into the calculation module 80 via input into the calculation module 80. Thus, in step 82, the calculation module 80 obtains the electromagnetically-measured value. In a second step 84, the ultrasound-measured value related to the axial thickness of the lens is received into the calculation module 80 via input into the calculation module 80. Thus, in step 84, the calculation module 80 obtains the ultrasound-measured value. In a third step 86, the calculation module 80 calculates a relationship value based upon the electromagnetically-measured value and the ultrasound-measured value. In a fourth step 88, the calculation module 80 determines a mechanical property value based upon the calculated relationship value, wherein the mechanical property value is related to a mechanical property of the lens. The mechanical property of the lens may be lens hardness, rigidity, or density, or the amount of energy needed in a phacoemulsification procedure. The calculation module 80 may determine that mechanical property value from a correlation function that correlates relationship values to mechanical property values. Additionally or alternatively, the calculation module 80 may determine that mechanical property value by looking up or calculating (e.g., by interpolation) that mechanical property value from a database that correlates relationship values to mechanical property values.

Figure 6:
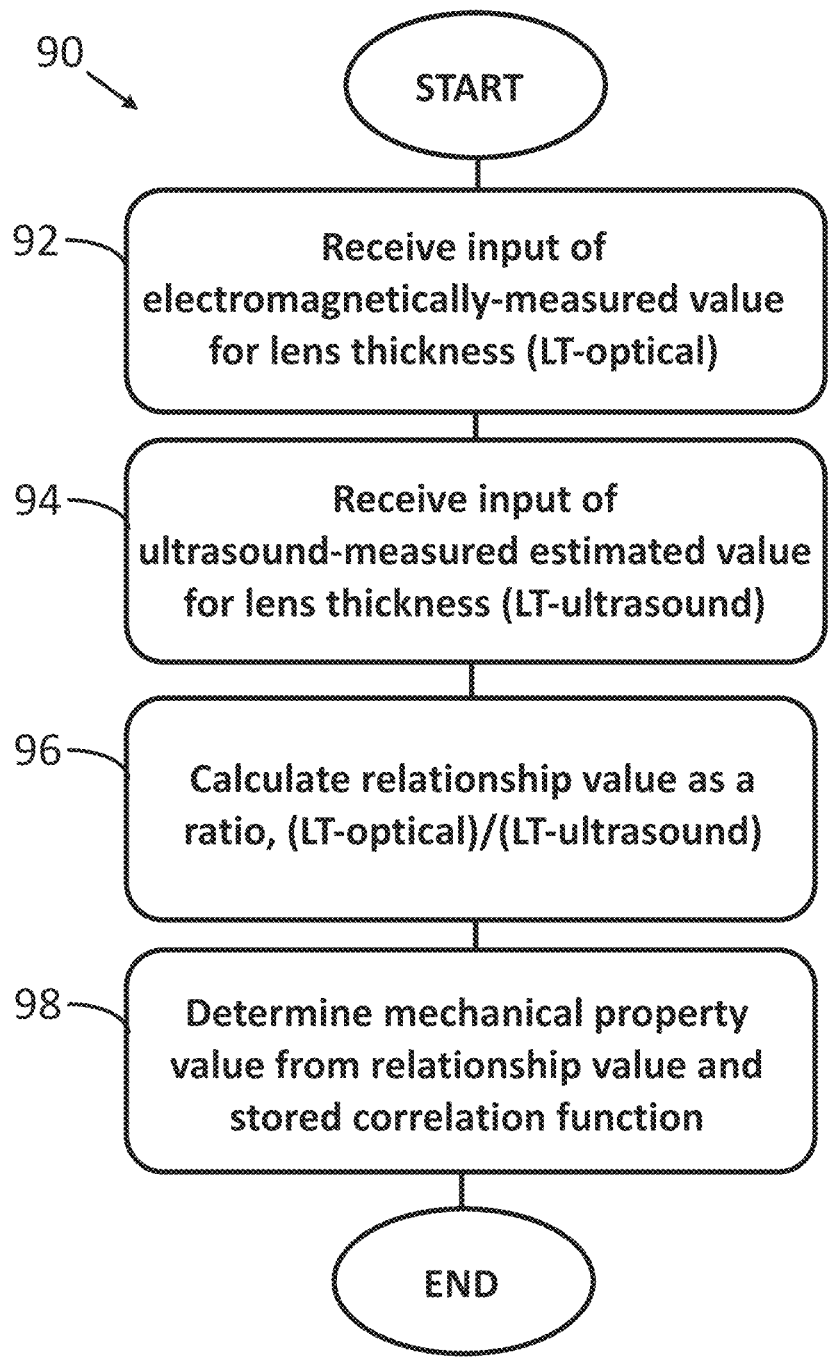
FIG. 6 shows a flowchart for steps in a second example of a calculation module.

FIG. 6 shows a flowchart for steps in a second calculation module 90. In a first step 92, the electromagnetically-measured value related to the axial thickness of the lens is received into the calculation module 90 via input into the calculation module 90, wherein the electromagnetically-measured value, LT-optical, is an electromagnetically-measured value for the axial thickness of the lens. Thus, in step 92, the calculation module 90 obtains the electromagnetically-measured value, LT-optical. In a second step 94, the ultrasound-measured value related to the axial thickness of the lens is received into the calculation module 90 via input into the calculation module 90, wherein the ultrasound-measured value, LT-ultrasound, is an ultrasound-measured estimated value for the axial thickness of the lens based upon an assumed velocity of the ultrasound signal. Thus, in step 94, the calculation module 90 obtains the ultrasound-measured value, LT-ultrasound. In a third step 96, the calculation module 90 calculates a relationship value based upon the electromagnetically-measured value and the ultrasound-measured value, wherein the relationship value R is the ratio of the electromagnetically-measured value for lens thickness, LT-optical, to the ultrasound-measured estimated value for lens thickness, LT-ultrasound, i.e., R=(LT-optical)/(LT-ultrasound). In a fourth step 98, the calculation module 90 determines a mechanical property value based upon the calculated relationship value R, wherein the mechanical property value is related to a mechanical property of the lens, such as lens hardness, rigidity, or density, or the amount of energy needed in a phacoemulsification procedure, determined from a correlation function that correlates relationship values to mechanical property values.

In a method using system 10, the steps described above may be performed. An electromagnetically-measured value related to the axial thickness of the lens is obtained, and an ultrasound-measured value related to the axial thickness of the lens is obtained. A relationship value is calculated based upon the electromagnetically-measured value and the ultrasound-measured value. Then, a mechanical property value is determined based upon the relationship value.

The mechanical property value or information related to the desired mechanical property may then be output to the user, for example shown on a computer display 68 or another display of the system, printed, or output to another system. A user (physician or operator) may use the mechanical property information to make determinations relating to patient procedure. For example, the user may use the mechanical property information to make determinations regarding the amount of phacoemulsification energy to use in a phacoemulsification procedure or may use the mechanical property information to make other determinations regarding phacoemulsification technique. The user may use the mechanical property information to optimize lens fragmentation pattern, to preselect the settings of the phacoemulsification procedure, and/or to make decisions regarding the surgical techniques to be used. In addition, having the mechanical property information prior to the procedure avoids surprise, such as finding that the lens is much harder than expected, which can increase risk associated with the procedure. By having information about the mechanical properties in advance, the procedure risk can be minimized, and outcome can be improved. As another example, the mechanical property information may show that the patient is not suitable for a phacoemulsification procedure. As yet another example, the mechanical property information may be used as a correlation factor in the IOL design formula, which can improve refractive outcomes.

It will be appreciated that the systems and methods as described herein provide advancements and advantages. For example, systems and methods as described herein have the ability to take all measurements in vivo and non-invasively. In addition, systems and methods as described herein can provide a user valuable information for use in patient care, as described above.

The above embodiments are meant as illustrative examples only. Other embodiments are possible within the scope of the disclosure and the appended claims.

What is claimed is:

1. A system for obtaining a pre-surgical characterization of a lens of an eye, the system comprising:
    an optical interferometer adapted to transmit electromagnetic energy into the lens of the eye and to capture reflected signals of that electromagnetic energy for obtaining an electromagnetically-measured value related to the axial thickness of the lens;
    an ultrasound biometer adapted to transmit an ultrasound signal into the lens of the eye and to capture reflected signals of that ultrasound signal for obtaining an ultrasound-measured value related to the axial thickness of the lens; and
    a calculation module comprising one or more processors and computer code stored in memory of the system and executable by the one or more processors of the system, the calculation module configured to:
    calculate, when executed by the one or more processors, a relationship value based upon the electromagnetically-measured value related to the axial thickness of the lens and the ultrasound-measured value related to the axial thickness of the lens;
    determine, when executed by the one or more processors, an amount of phacoemulsification energy needed in a phacoemulsification procedure based upon the calculated relationship value; and
    generate an output for a physician related to the amount of phacoemulsification energy needed in a phacoemulsification procedure.

2. A system as recited in claim 1, wherein the electromagnetically-measured value is an electromagnetically-measured value for the axial thickness of the lens.

3. A system as recited in claim 1, wherein the ultrasound-measured value is an ultrasound-measured estimated value for the axial thickness of the lens based upon an assumed velocity of the ultrasound signal.

4. A system as recited in claim 1, wherein the electromagnetically-measured value is an electromagnetically-measured value for the axial thickness of the lens, the ultrasound-measured value is an ultrasound-measured estimated value for the axial thickness of the lens based upon an assumed velocity of the ultrasound signal, and the relationship value is a ratio of the electromagnetically-measured value and the ultrasound-measured value.

5. A system as recited in claim 1, wherein the electromagnetic energy transmitted by the optical interferometer is laser light.

6. A system as recited in claim 1, wherein the ultrasound biometer is an A-scan ultrasound biometer.

7. A system as recited in claim 1, wherein the optical interferometer is adapted to operate non-invasively to transmit the electromagnetic energy into the lens of the eye and to capture reflected signals of that electromagnetic energy.

8. A system as recited in claim 1, wherein the ultrasound biometer is adapted to operate non-invasively to transmit the ultrasound signal into the lens of the eye and to capture reflected signals of that ultrasound signal.

9. A system as recited in claim 1, wherein the system is adapted to operate non-invasively to measure the electromagnetically-measured value in vivo and the ultrasound-measured value in vivo.

\* \* \* \* \*